(12) United States Patent
Sakata et al.

(10) Patent No.: US 12,029,551 B2
(45) Date of Patent: Jul. 9, 2024

(54) DROWSINESS SIGN NOTIFICATION SYSTEM

(71) Applicant: TOYOTA JIDOSHA KABUSHIKI KAISHA, Toyota (JP)

(72) Inventors: Takuya Sakata, Tokyo-to (JP); Koichiro Yamauchi, Tokyo-to (JP); Masataka Sano, Tokyo-to (JP); Hiromi Nemoto, Tokyo-to (JP); Shunichiroh Sawai, Tokyo-to (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 476 days.

(21) Appl. No.: 17/351,394

(22) Filed: Jun. 18, 2021

(65) Prior Publication Data
US 2022/0000394 A1  Jan. 6, 2022

(30) Foreign Application Priority Data

Jul. 1, 2020  (JP) .................................. 2020-114155

(51) Int. Cl.
*A61B 5/18* (2006.01)
*A61B 5/11* (2006.01)

(52) U.S. Cl.
CPC ............. *A61B 5/1103* (2013.01); *A61B 5/18* (2013.01)

(58) Field of Classification Search
CPC .............. B60K 28/06; B60K 28/066; B60W 2040/0818; B60W 2040/0872; B60W 2040/0827; B60W 50/14; A61B 5/18
See application file for complete search history.

(56) References Cited

U.S. PATENT DOCUMENTS

| | | | |
|---|---|---|---|
| 2010/0090839 A1 | 4/2010 | Omi | |
| 2015/0314681 A1* | 11/2015 | Riley, Sr. | ............ A61B 5/7455 340/576 |
| 2016/0001781 A1* | 1/2016 | Fung | ....................... G07C 9/37 701/36 |
| 2016/0304099 A1 | 10/2016 | Hatakeyama | |
| 2018/0012090 A1* | 1/2018 | Herbst | ................... G06V 40/20 |
| 2019/0332106 A1* | 10/2019 | Belloni Mourao | ... B60W 40/08 |
| 2021/0291839 A1* | 9/2021 | Hutchings | ................ A61B 5/18 |

FOREIGN PATENT DOCUMENTS

| | | |
|---|---|---|
| CN | 107490485 A | 12/2017 |
| JP | H07108848 A | 4/1995 |
| JP | 2008-210375 A | 9/2008 |
| JP | 2016202419 A | 12/2016 |
| JP | 2018116650 A | 7/2018 |
| JP | 2019-016178 A | 1/2019 |

* cited by examiner

*Primary Examiner* — Benyam Haile
(74) *Attorney, Agent, or Firm* — Dickinson Wright, PLLC

(57) ABSTRACT

A drowsiness sign notification system that gives a drowsiness sign notice to a driver that shows a drowsiness sign includes a driver monitor and a controller. The driver monitor detects the driver state being a state of the driver. The controller executes a drowsiness level estimation process in which a drowsiness level of the driver from a plurality of drowsiness levels based on the driver state. And, the controller executes an accumulation process in which a drowsiness point that is numerical value corresponding to the drowsiness level estimated in the drowsiness level estimation process is accumulated. Then, when an accumulation value of the drowsiness point calculated in the accumulation process exceeds a predetermined threshold, the controller determines that the driver shows the drowsiness sign.

5 Claims, 7 Drawing Sheets

| DROWSINESS LEVEL | D0 (NO DROWSINESS) | D1 (SLIGHTLY SLEEPY) | D2 (SLEEPY) | D3 (QUITE SLEEPY) | D4 (VERY SLEEPY) |
|---|---|---|---|---|---|
| DROWSINESS ACTION | • TALKING<br>• CHECKING OPERATIONS | • DECREASE IN BLINKING SPEED<br>• NOT CONSTANT IN BLINKING CYCLE | • FREQUENT BLINKING<br>• HEAD MOVEMENT<br>• A LITTLE HEAVY EYELIDS | • HALF-CLOSED EYES<br>• HEAVY EYELIDS<br>• CLOSING EYELIDS FOR SHORT TIME<br>• LONG YAWN | • CLOSING EYELIDS |

| DROWSINESS LEVEL | D0 (NO DROWSINESS) | D1 (SLIGHTLY SLEEPY) | D2 (SLEEPY) | D3 (QUITE SLEEPY) | D4 (VERY SLEEPY) |
|---|---|---|---|---|---|
| DROWSINESS ACTION | • TALKING<br>• CHECKING OPERATIONS | • DECREASE IN BLINKING SPEED<br>• NOT CONSTANT IN BLINKING CYCLE | • FREQUENT BLINKING<br>• HEAD MOVEMENT<br>• A LITTLE HEAVY EYELIDS | • HALF-CLOSED EYES<br>• HEAVY EYELIDS<br>• CLOSING EYELIDS FOR SHORT TIME<br>• LONG YAWN | • CLOSING EYELIDS |

FIG. 2

DROWSINESS SIGN NOTIFICATION SYSTEM

BACKGROUND

Technical Field

The present disclosure relates to a technique that notifies that a driver of a vehicle shows a drowsiness sign.

Background Art

Patent Literature 1 discloses a state detection device that detects a state at plural levels. This state detection system detects a state level of an operator by determining the state level to corresponding to the each plural level based on an operation amount and an appearance frequency.

Patent Literature 2 discloses a drowsiness detection device that detects drowsiness of a driver while driving. This drowsiness detection device, when the processing that resets a threshold for determining drowsiness is executed (e.g., when the driving is suspended), avoids unnecessary threshold resetting by judging whether to reset by considering necessity.

In addition, the following Patent Literature 3 is disclosed as a literature showing the technical level in this technical field.

LIST OF RELATED ART

Patent Literature 1: Japanese Laid-Open Patent Application Publication No. JP-2018-116650
Patent Literature 2: Japanese Laid-Open Patent Application Publication No. JP-2016-202419
Patent Literature 3: Japanese Laid-Open Patent Application Publication No. JP-H07-108848

SUMMARY

When estimating drowsiness from a state of a driver, it is difficult to accurately estimate drowsiness of the driver every moment by complicated actions of the driver while driving, and it may cause misestimating. Therefore, if a drowsiness sign notice is given to the driver when the estimated drowsiness exceeds a certain level, the drowsiness sign notice may be given at unnecessary timing by misestimating, and it may cause annoyance sense to the driver.

An object of the present disclosure is to provide a drowsiness sign notification system that suppress the drowsiness sign notice is given at unnecessary timing, and suppress the annoyance sense to the driver.

The present disclosure is directed to a drowsiness sign notification system that gives a drowsiness sign notice to a driver that shows a drowsiness sign.

The drowsiness sign notification system includes:
a driver monitor configured to detect a driver state being a state of the driver; and
a controller configured to make a request of the drowsiness sign notice based on the driver state.
Wherein, the controller is configured to:
execute a drowsiness level estimation process in which a drowsiness level of the driver is estimated based on the driver state from a plurality of drowsiness levels, each of which shows a degree of drowsiness and is classified by the degree of drowsiness;
execute an accumulation process in which a drowsiness point is accumulated.

Wherein, each of the drowsiness levels is a degree of drowsiness of the driver and is classified by the degree of drowsiness. The drowsiness point is a numerical value corresponding to the drowsiness level estimated in the drowsiness level estimation process.

And, the controller is further configured to execute a drowsiness sign determination process in which it is determined that the driver shows the drowsiness sign when an accumulation value of the drowsiness point calculated in the accumulation process exceeds a predetermined threshold.

In the drowsiness level estimation process, a drowsiness action is corresponded to each of the drowsiness levels, wherein the controller may be configured to:
detect the drowsiness action corresponding to respective drowsiness levels based on the drowsiness state; and
when the drowsiness action is detected, estimate the drowsiness level of the driver as the drowsiness level corresponding to the detected drowsiness action.

In the drowsiness level estimation process, the controller may be configured to:
detect at the top priority the drowsiness action corresponding to the drowsiness level that means the driver has no drowsiness, after that, detect the drowsiness action in the order of the drowsiness level with the higher degree of drowsiness.

The controller may be configured to:
store a frequency distribution of the drowsiness level estimated in the drowsiness level estimation process; and
dynamically change the drowsiness point corresponding to the estimated drowsiness level based on the frequency distribution.

The controller may be configured to:
calculate a reliability for the drowsiness level estimated in the drowsiness level estimation process; and
change the drowsiness point to be accumulated in the accumulation process based on the calculated reliability.

According to the present disclosure, the controller accumulates the drowsiness point corresponding to the estimated drowsiness level of the driver, and the drowsiness sign notice is given when the accumulation value of the drowsiness point exceeds the predetermined threshold. It is thus possible to suppress giving the drowsiness sign notice at unnecessary timing and suppress annoyance sense to the driver.

Furthermore, the controller may be configured to change the drowsiness point based on the frequency distribution or the calculated reliability. It is thus possible to consider the dispersion of the drowsiness actions by influence of the driver's individual differences and driving environments. Then, it is possible to improve the accuracy of estimation.

BRIEF DESCRIPTION OF DRAWINGS

FIG. 2 is a table showing an example of a drowsiness action corresponding to each of drowsiness levels.

EMBODIMENTS

Embodiments of the present disclosure will be described with reference to the accompanying drawings.

1. Configuration

Figure 1:
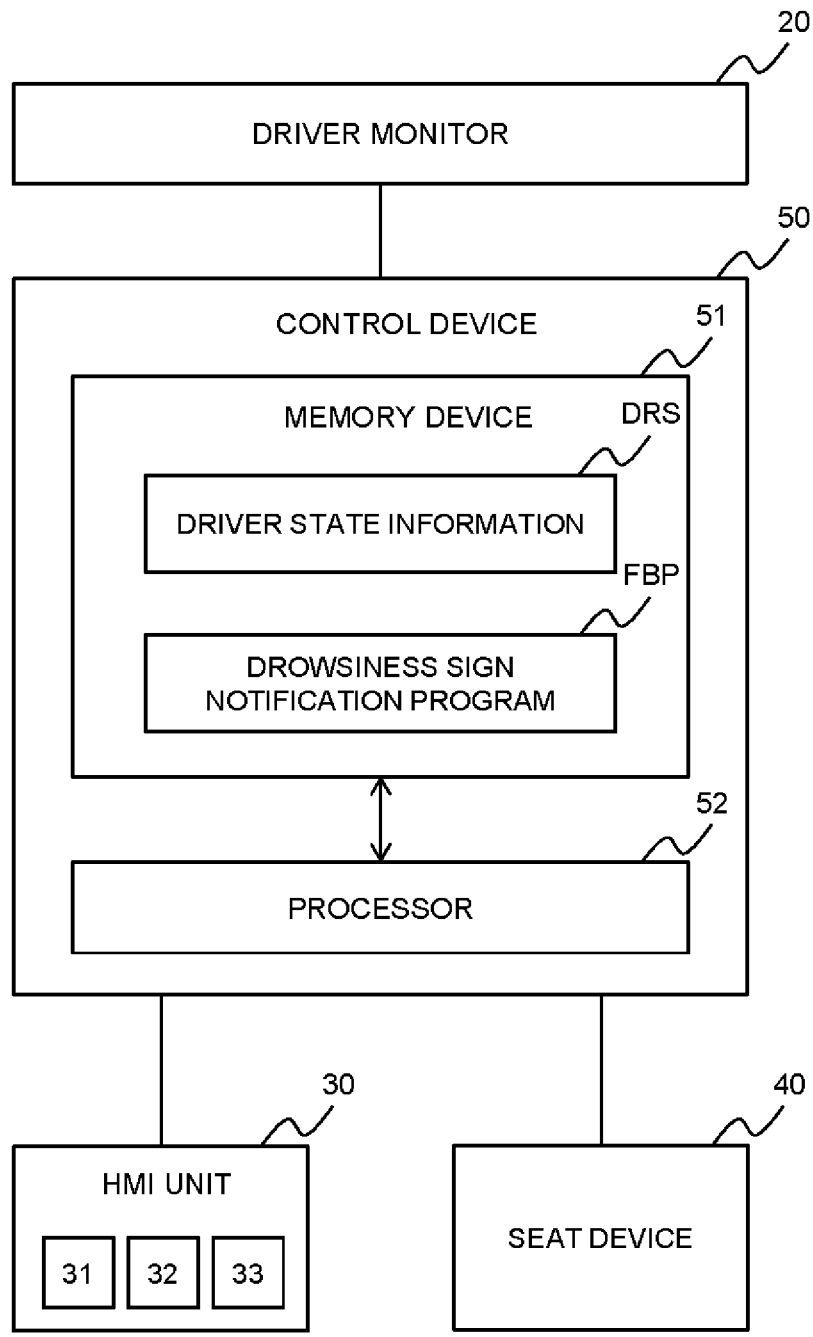
FIG. 1 is a block diagram showing a configuration example of a drowsiness sign notification system according to an embodiment of the present disclosure.

FIG. 1 is a block diagram showing a configuration example of a drowsiness sign notification system 10 according to the present embodiment. The drowsiness sign notification system 10 includes a driver monitor 20, an HMI (Human Machine Interface) unit 30, a seat device 40, and a control device (controller) 50. The driver monitor 20, the HMI unit 30, and the seat device 40 are connected to the control unit 50 by a vehicle network (e.g., CAN (Control Area Network)).

The driver monitor 20 is installed on the vehicle and detects a state of the driver (hereinafter, also referred to as a driver state). The driver monitor 20 is installed at the place where it can capture the driver's face in the front of the driver seat, for example, at the upside of a steering column, or at near a rear view monitor. The driver state detected by the driver monitor 20 is, for example, the facial expression such as a degree of eye opening, a degree of mouth opening, a face orientation, a line of sight, and the like of the driver. These detected driver states are stored in a memory device 51 (described later) as a driver state information DRS.

The control device (controller) 50 includes the memory device 51 and a processor 52. Typically, the control device 50 is an ECU (Electronic Control Unit) installed on the vehicle. The memory device 51 includes a RAM (Random Access Memory) for storing a data temporarily, and a ROM (Read Only Memory) for storing a control program that can be executed by the processor 52 and various data related to the control program. The memory device 51 stores at least the driver state information DRS as the data. And, the memory device 51 at least stores a drowsiness sign notification program FBS as the control program. The processor 52 executes a program by reading out the control program and the data from memory device 51, and generates various control signals.

The processor 52 at least executes the program by reading out the driver state information DRS and the drowsiness sign notification program FBS from memory device 51. Thus, the control device 50 determines whether the driver shows a drowsiness sign based on the driver state information DRS, and makes a drowsiness sign notification request to the HMI unit 30 or the seat device 40.

The HMI unit 30 is an interface that outputs information to the driver and receives input of information form the driver. The HMI unit 30 includes a visual device 31, a speaker 32, and an input device 33.

The visual device 31 is, for example, a display installed in an instrument panel, a HUD (Head-Up Display), a luminescent device (e.g., LED (Light Emitting Diode)), and the like.

The speaker 32 is a device that outputs audio. The input device 33 is, for example, a touch panel, a button, a microphone, and the like.

The HMI unit 30 also functions as a drowsiness sign notification device. The HMI unit gives a drowsiness sign notice, when the HMI unit 30 receives the drowsiness sign notification request from the control device 50.

The drowsiness sign notice given by the HMI unit 30 is what encouraging the awareness of the driver by display or sound. For example, the HMI unit 30 displays a text message (e.g., "Are you sleepy?") on the visual device 31, displays a flashing display on the visual device 31, or outputs an audio message (e.g., "Are you sleepy?") through the speaker 32.

The seat device 40 is a device related to a seat on which the driver sits. For example, the seat device 40 is an actuator that vibrates a seat belt of the seat. As another example, the seat device 40 has a refresh seat function to press a back and a thigh of the driver by inflating an air bag installed in a seatback and a seat cushion of the seat.

The seat device 40 also functions as the drowsiness sign notification device. The seat device 40 gives the drowsiness sign notice, when the seat device 40 receives the drowsiness sign notification request form the control device 50.

The drowsiness sign notice given by the seat device 40 is what encouraging the awareness of the driver by stimulating the driver. For example, the seat device 40 operates the actuator to vibrate the seat belt, or makes the refresh seat function work.

2. Drowsiness Level

Hereinafter, a plurality of drowsiness levels that is a prerequisite for the drowsiness sign notice will be described. Each of the drowsiness levels is a degree of drowsiness and is classified by the degree of drowsiness. For example as shown in FIG. 2, each of the drowsiness levels is classified in 5 ranks by D0 to D4 in the order of the low degree of drowsiness.

A D0 drowsiness level is a drowsiness level that means the driver has no drowsiness, a D1 drowsiness level is a drowsiness level that means the driver is slightly sleepy, a D2 drowsiness level is a drowsiness level that means the driver is sleepy, a D3 drowsiness level is a drowsiness level that means the driver is quite sleepy, and a D4 drowsiness level is a drowsiness level that means the driver is very sleepy.

As described later, a drowsiness level of the driver is estimated from the plurality of drowsiness levels by detecting a drowsiness action that is corresponded to each of the drowsiness levels. The drowsiness action is detected based on the drowsiness state information DRS in a predetermined time (e.g., 10 seconds) (hereinafter, also referred to as an estimating target time). Examples of the drowsiness action corresponding to respective drowsiness levels are shown in FIG. 2. These correspondences can be given in advance by study and research.

The drowsiness action is detected by analyzing the data included in the driver state information DRS (e.g., the degree of eye opening, the degree of mouth opening, the face orientation, and like that). For example, the drowsiness action "frequent blinking" corresponding to the D2 drowsiness level is detected when the data of the degree of eye opening includes more than a predetermined number of a blinking event (e.g., the degree of eye opening changes in a short time) in the estimating target time. As another example, the drowsiness action "long yawn" of the D3 drowsiness level is detected when the data of the degree of mouth opening includes the degree exceeding a predetermined value that continues more than a predetermined time.

3. Estimating Drowsiness Level

Figure 3:
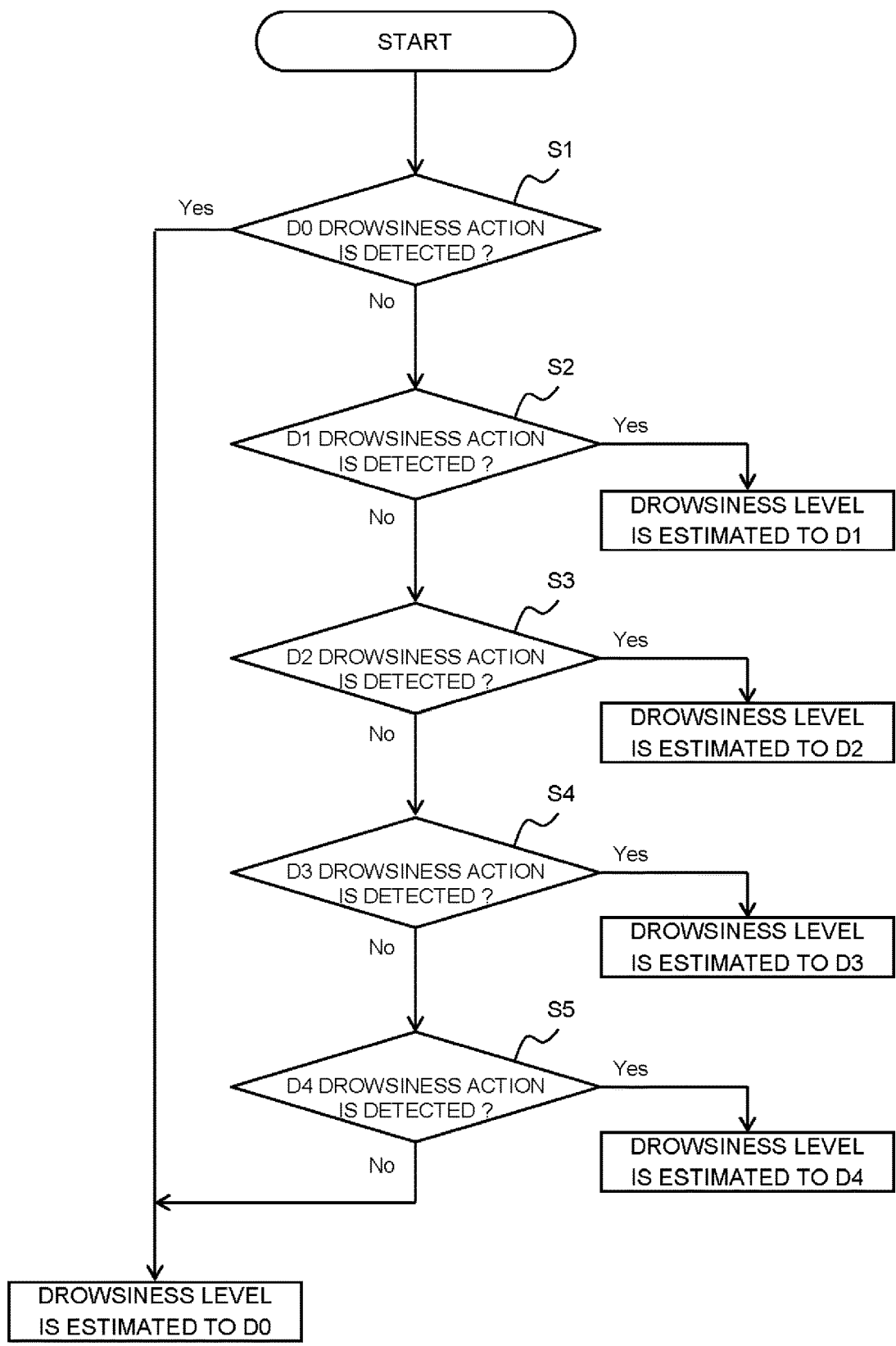
FIG. 3 is a drawing showing a decision tree when estimating the drowsiness level of a driver in the drowsiness sign notification system according to an embodiment of the present disclosure.

The drowsiness level of the driver is estimated from the plurality of drowsiness levels by detecting the drowsiness action corresponding to respective drowsiness levels. FIG. 3 is a drawing showing a decision tree when estimating the drowsiness level of the driver by executing the drowsiness sign notification program FBP according to an embodiment of the present disclosure.

In Step S1, the control device 50 executes a process that determines whether or not the drowsiness action corresponding to the D0 drowsiness level is detected. When the drowsiness action corresponding to the D0 drowsiness level is detected (Step S1; Yes), the control device 50 estimates the drowsiness level of the driver as the D0 drowsiness level. When the drowsiness action corresponding to the D0 drowsiness level is not detected (Step S1; No), the processing proceeds to the Step S2.

In Step S2, the control device 50 executes a process that determines whether or not the drowsiness action corresponding to the D4 drowsiness level is detected. When the drowsiness action corresponding to the D4 drowsiness level is detected (Step S2; Yes), the control device 50 estimates the drowsiness level of the driver as the D4 drowsiness level. When the drowsiness action corresponding to the D4 drowsiness level is not detected (Step S2; No), the processing proceeds to the Step S3.

In Step S3, the control device 50 executes a process that determines whether or not the drowsiness action corresponding to the D3 drowsiness level is detected. When the drowsiness action corresponding to the D3 drowsiness level is detected (Step S3; Yes), the control device 50 estimates the drowsiness level of the driver as the D3 drowsiness level. When the drowsiness action corresponding to the D3 drowsiness level is not detected (Step S3; No), the processing proceeds to the Step S4.

In Step S4, the control device 50 executes a process that determines whether or not the drowsiness action corresponding to the D2 drowsiness level is detected. When the drowsiness action corresponding to the D2 drowsiness level is detected (Step S4; Yes), the control device 50 estimates the drowsiness level of the driver as the D2 drowsiness level. When the drowsiness action corresponding to the D2 drowsiness level is not detected (Step S4; No), the processing proceeds to the Step S5.

In Step S5, the control device 50 executes a process that determines whether or not the drowsiness action corresponding to the D1 drowsiness level is detected. When the drowsiness action corresponding to the D1 drowsiness level is detected (Step S5; Yes), the control device 50 estimates the drowsiness level of the driver as the D1 drowsiness level. When the drowsiness action corresponding to the D1 drowsiness level is not detected (Step S5; No), the control device 50 estimates the drowsiness level of the driver as the D0 drowsiness level.

As described in FIG. 3, the control device 50 executes the process to detect the drowsiness action corresponding to respective drowsiness levels. Then, when the drowsiness action is detected, the control device 50 estimates the drowsiness level of the driver as the drowsiness level corresponding to the detected drowsiness action. Therefore, for example, when the drowsiness action corresponding to the D0 and D4 drowsiness level is not detected and the drowsiness action corresponding to the D3 drowsiness level is detected, the control device 50 estimates the drowsiness level of the driver as the D3 drowsiness level without detecting the drowsiness action corresponding to D1 and D2 drowsiness level. Also, when any drowsiness action is not detected, the control device 50 estimates the drowsiness level of the driver as the D0 drowsiness level.

As shown in FIG. 3, the control device 50 executes the process to detect at the top priority the drowsiness action corresponding to the D0 drowsiness level (shows the driver has no drowsiness), after that, detect the drowsiness action in the order of the drowsiness level with the higher degree of drowsiness. Detecting the drowsiness action corresponding to the lowest and the highest drowsiness level preferentially as described above makes it possible to suppress misestimating the drowsiness level of the driver.

4. Calculating Drowsiness Degree

Hereinafter, a drowsiness degree will be described. The control device 50 estimates the drowsiness level of the driver in a predetermined control cycle, and gets a drowsiness point corresponding to the estimated drowsiness level.

Figure 4:
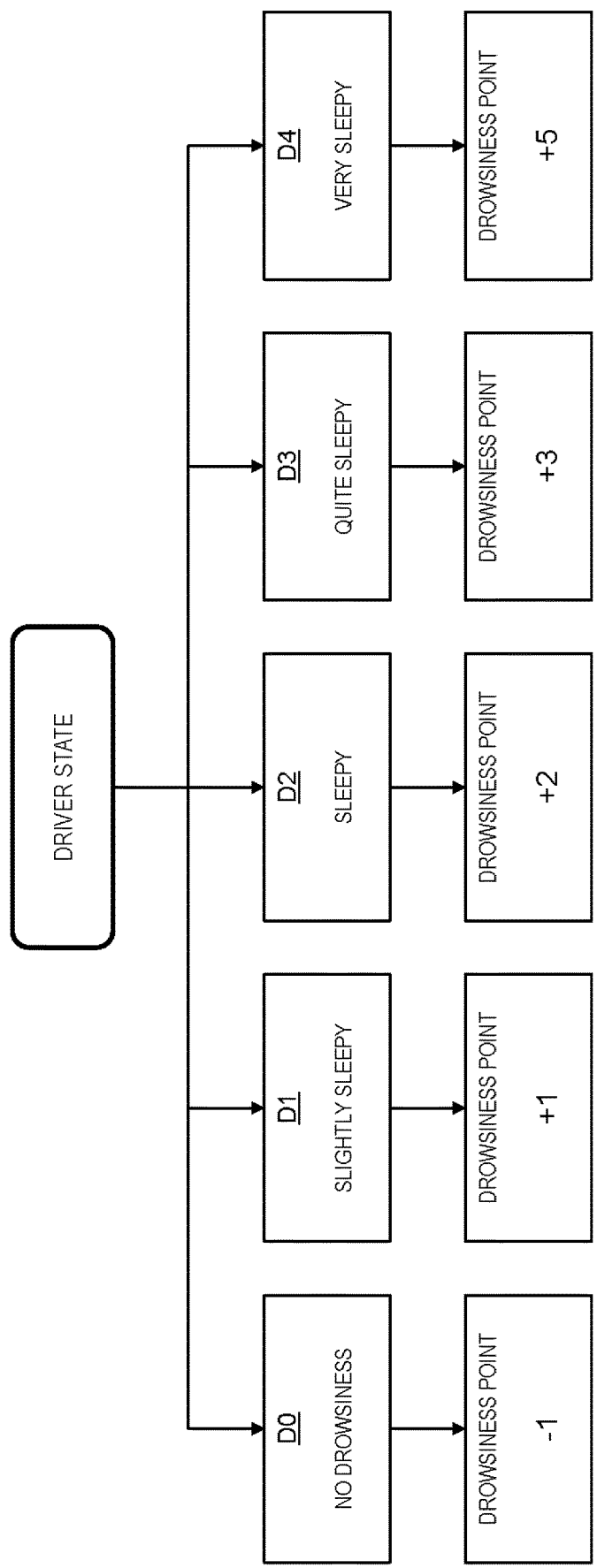
FIG. 4 is a drawing showing an example of a drowsiness point corresponding to the estimated drowsiness level.

The drowsiness point is a numerical value corresponding to the estimated drowsiness level of the driver. An example of the drowsiness point corresponding to the estimated drowsiness level of the driver is shown in FIG. 4. In FIG. 4, the drowsiness point corresponding to the D0 drowsiness level is minus 1, the drowsiness point corresponding to the D1 drowsiness level is plus 1, the drowsiness point corresponding to the D2 drowsiness level is plus 2, the drowsiness point corresponding to the D3 drowsiness level is plus 3, the drowsiness point corresponding to the D4 drowsiness level is plus 5. That is, the higher the estimated drowsiness level is, the higher the drowsiness point corresponding to the estimated drowsiness level is. Wherein, the drowsiness point corresponding to the estimated drowsiness level may be given differently depending on the situation in which the drowsiness sign notification system 10 works.

Figure 5:
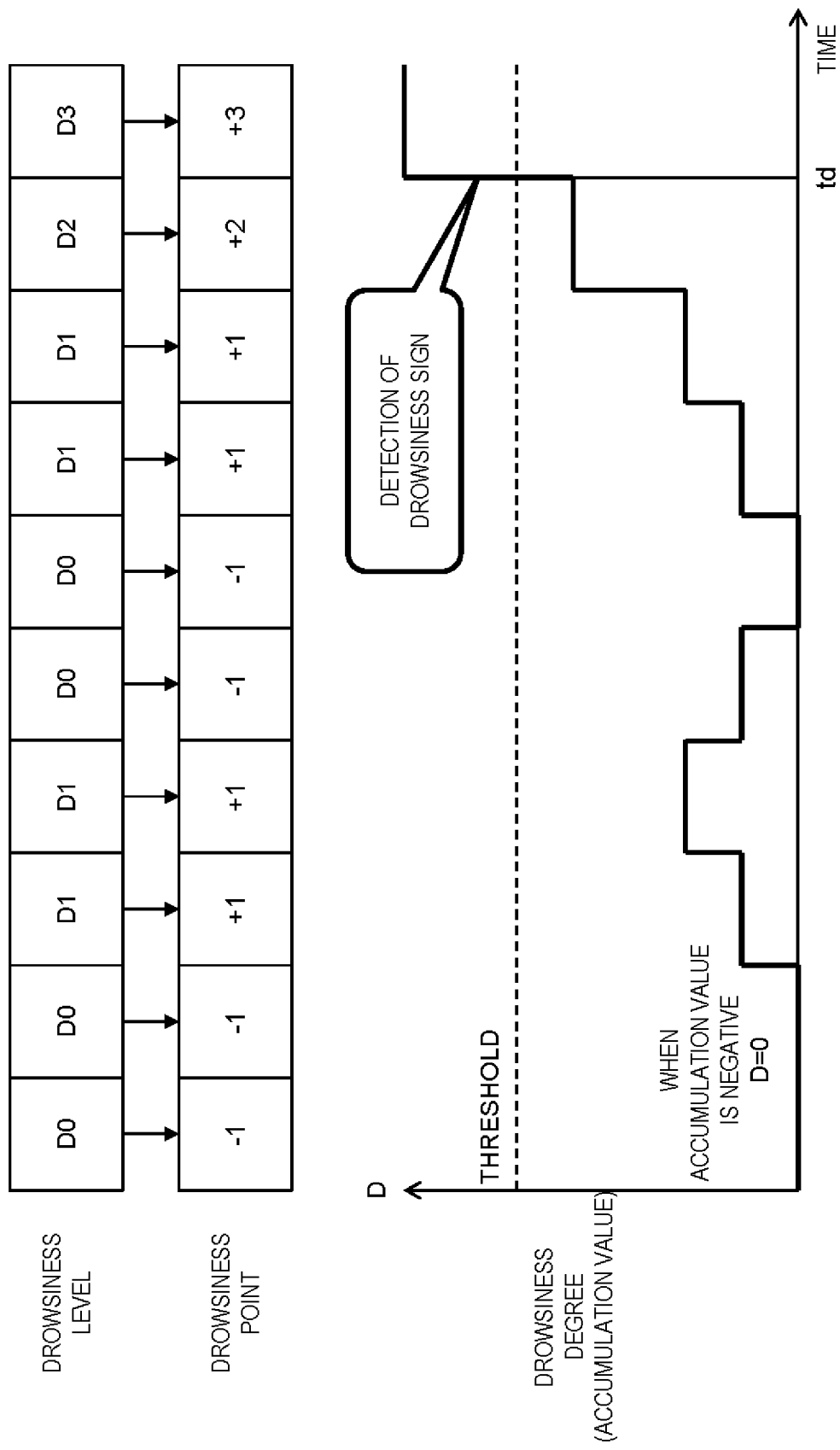
FIG. 5 is a drawing showing an outline of a processing of a drowsiness sign notification program.

The control device 50 gets the drowsiness point in the predetermined control cycle, and accumulates the drowsiness point sequentially as shown in FIG. 5. The control device 50 calculates an accumulation value of the drowsiness point (a drowsiness degree D). The drowsiness degree D shows intensity of drowsiness of the driver. Wherein, when the result of the calculation is negative, the drowsiness degree D is set to zero.

In FIG. 4, because the drowsiness point corresponding to the D0 drowsiness level is minus 1, the result of the calculation can be negative. As shown in FIG. 5, when the result of the calculation is negative, the drowsiness degree D is set to zero. In addition, right after the control device 50 starts to execute the program, the drowsiness degree D is zero.

The drowsiness degree D is given a predetermined threshold. When the drowsiness degree D exceeds the predetermined threshold (in FIG. 5, at the time td), the control device 50 determines that the driver shows the drowsiness sign. That is, the control device 50 determines whether the driver shows the drowsiness sign comprehensively from the transition of the drowsiness level of the driver. Wherein, the predetermined threshold may be given appropriately. However, in order to improve the certainty of preventing doze driving, the predetermined threshold should be a value smaller than the drowsiness point corresponding to the D4 drowsiness level.

When the drowsiness degree D exceeds the predetermined threshold, the control device 50 determines that the driver shows the drowsiness sign and makes the drowsiness sign notification request.

5. Processing

Figure 6:
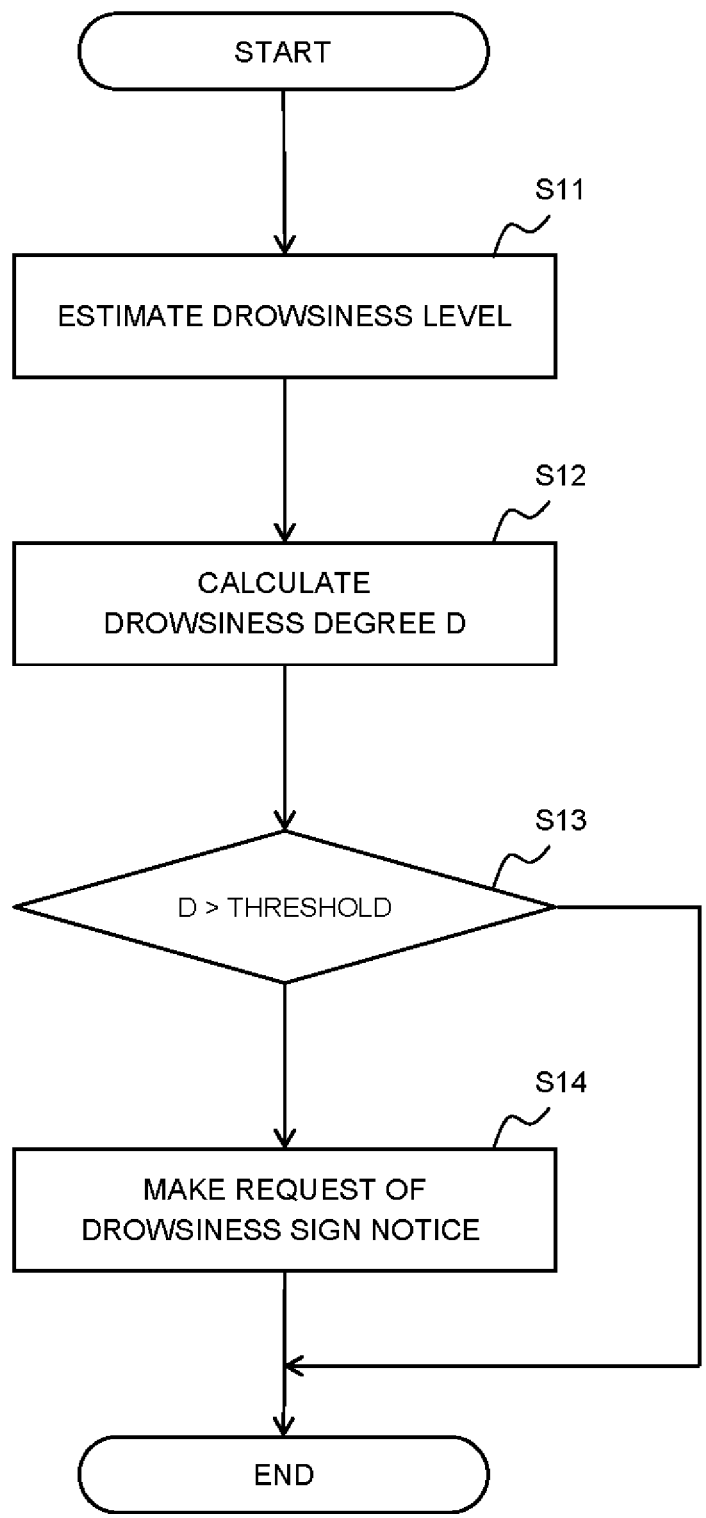
FIG. 6 is a flow chart showing a processing executed in the drowsiness sign notification system according to an embodiment of the present disclosure.

The control device 50 according to the present embodiment executes the processes that determine whether the driver shows the drowsiness sign and make the drowsiness sign notification request. A processing for these processes is realized by the drowsiness sign notification program FBP is executed. FIG. 6 is a flow chart showing the processing that is realized by the drowsiness sign notification program FBP is executed. Wherein, the processing shown in FIG. 6 is executed repeatedly in a predetermined control cycle of the control device 50.

In Step S11 (a drowsiness level estimation process), the control device 50 estimates the drowsiness level of the driver from the plurality of drowsiness levels based on the driver state information DRS. As described above, the drowsiness level of the driver is estimated by detecting the drowsiness action corresponding to respective drowsiness level based on the decision tree shown in FIG. 3.

In Step S12 (an accumulation process), the control device 50 accumulates the drowsiness point and calculates the drowsiness degree D. The control device 50 gets the drowsiness point corresponding to the drowsiness level estimated in Step S11, and sequentially accumulates the drowsiness point that is get every control cycle. Then, the control device 50 calculates the drowsiness degree D.

In Step S13 (a drowsiness sign determination process), the control device 50 determines whether or not the drowsiness degree D calculated in Step S12 exceeds the predetermined threshold. When the drowsiness degree D exceeds the predetermined threshold, the control device 50 determines that the driver shows the drowsiness sign. Wherein, the predetermined threshold can be adjusted according to the drowsiness sign notification system 10, and it is given to the program in advance.

When the control device 50 determines that the driver shows the drowsiness sign (Step S13; Yes), the processing proceeds to Step S14. Then, the control device 50 makes the drowsiness sign notification request (Step S14), and the processing in the current control cycle ends. When the control device 50 determines that the driver doesn't show the drowsiness sign (Step S13; No), the processing in the current control cycle ends.

6. Effect

As described above, according to the drowsiness sign notification system 10 according to the present embodiment, the control device 50 estimates the drowsiness level of the driver by detecting the drowsiness action corresponding to respective drowsiness levels, and calculates the drowsiness degree D by accumulating the drowsiness point corresponding to the estimated drowsiness level. Then, when the drowsiness degree D exceeds the predetermined threshold, the control device 50 determines that the driver shows the drowsiness and makes the drowsiness sign notification request. It is thus possible to suppress giving the drowsiness sign notice at unnecessary timing and suppress annoyance sense to the driver.

7. Modification

The drowsiness sign notification system 10 according to the present embodiment may be modified as follows.

7-1. First Modification Example

The memory device 51 may store a predetermined frequency distribution of the drowsiness level for reference (hereinafter, also referred to as a base frequency distribution), and a frequency distribution of the drowsiness level estimated in the drowsiness level estimation process (hereinafter, also referred to as an actual frequency distribution). And, the control device 50 may dynamically change the drowsiness point that is get in the accumulation process by comparing the base frequency distribution and the actual frequency distribution.

The base frequency distribution and the actual frequency distribution show the frequency of respective drowsiness levels. Wherein, an example of the base frequency distribution is a frequency distribution that is given experimentally as a typical driving.

The control device 50 dynamically change the drowsiness point that is get in the accumulation process by the result of the comparing the base frequency distribution and the actual frequency distribution. For example, the control device 50 change the drowsiness point as follows.

Figure 7:
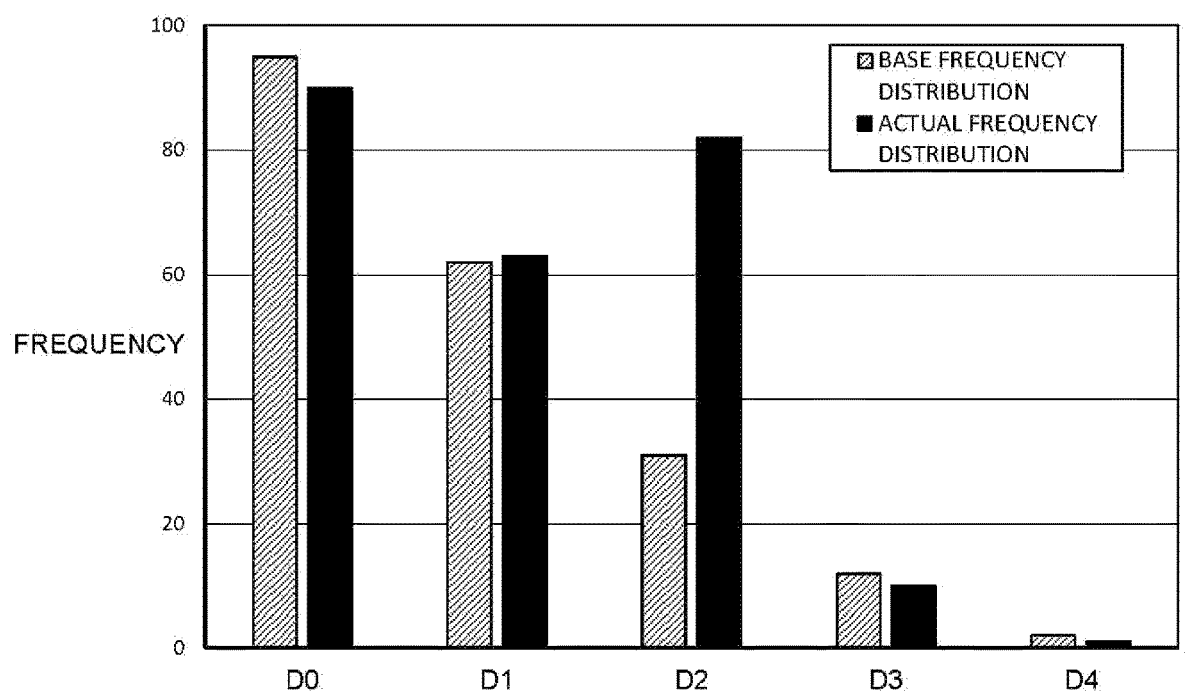
FIG. 7 is a graph showing an example of comparing a base frequency distribution and an actual frequency distribution.

FIG. 7 is a graph showing an example of comparing the base frequency distribution and the actual frequency distribution. In FIG. 7, only the frequency of the D2 drowsiness level in the actual frequent distribution is higher than that in the base frequent distribution. In that case, it is possible to have estimated the D2 drowsiness level incorrectly by characteristic actions of the driver. Therefore, the control device 50 lower the drowsiness point corresponding to the D2 drowsiness level.

For example, when the drowsiness point is given as shown in FIG. 4, the control device 50 changes the drowsiness point corresponding to the D2 drowsiness level from plus 2 to plus 0.5. The control device 50 may change the drowsiness point according to a function of the differences of the comparing. Or, the control device 50 may change the drowsiness point in order to balance the base frequency distribution and the actual frequency distribution.

Changing the drowsiness point that is get in the accumulation process as described above makes it possible to suppress influence of the misestimating.

As another case, when the frequency of the high drowsiness level (e.g., the D3 drowsiness level and the D4 drowsiness level) in the actual frequency distribution is higher in specific situations (e.g., the following situations C1 to C4) than that of the base drowsiness level, the control device 50 raises the drowsiness point corresponding to the high drowsiness level.

C1: When driving in a time zone that is commonly considered to be the peak of drowsiness (e.g., from 2:00 pm to 4:00 pm and from 2:00 am to 4:00 am).

C2: When the driving time is long (e.g., longer than 2 hours).

C3: When driving in an area where the accident by doze driving happens frequently.

C4: When driving on a road that tends to increase drowsiness.

It is thus possible to improve the accuracy of the estimation, because the control device 50 is, in situations where drowsiness tends to increase, more likely to determine that the driver shows the drowsiness.

Wherein, whether or not the current situation is a specific situation can be determined by time information, map information, position information, and the like get by the control device 50 from the vehicle network. Especially, whether or not the current driving road is a road corresponding to the situation C4 may be determined by getting information of the drowsiness level estimated on the current driving road by cars that adopt the drowsiness sign notification system 10.

7-2. Second Modification Example

The control device 50 may calculate a reliability for the drowsiness level estimated in the drowsiness level estimation process, and change the drowsiness point to be accumulated in the accumulation process according to the calculated reliability.

The reliability may be calculated following viewpoint P1 to P3.

P1: A certainty of the detected drowsiness action.
P2: A number of the detected drowsiness action.
P3: A situation where the drowsiness action is detected.

According to the viewpoint P1, the reliability for the drowsiness level is calculated by the certainty of the detected drowsiness action. As an example, consider that the drowsiness action "long yawn" is detected based on the driver state information DRS. In this case, as described above, when the data of the degree of mouth opening includes the degree exceeding the predetermined value that continues more than a predetermined time, the control device 50 detect the drowsiness action "long yawn". Therefore, it can be said that the larger the degree of the mouth opening and the longer the duration, the higher the certainty of the detected drowsiness action. Then, when the drowsiness action "long yawn" is detected, the control device 50 can calculate the reliability by evaluating the degree of the mouth opening and the duration.

As another example, when the drowsiness action "closing eyelids" is detected, the longer the eye lids are closed, the higher the control device 50 calculate the reliability. As yet another example, when the drowsiness action "frequent blinking" is detected, the slower the blinking speed is, the higher the control device 50 calculates the reliability.

According to the viewpoint P2, the larger the number of the detected drowsiness action, the higher the control device 50 calculates the reliability for the drowsiness level. For example, when the control device 50 detect both the drowsiness action "head movement" (shown in FIG. 2) and the drowsiness action "a little heavy eyelids" (shown in FIG. 2), the control device 50 calculates the higher reliability for the D2 drowsiness level.

According to the viewpoint P3, when the drowsiness action is detected in a specific situation, the higher the control device 50 calculates the reliability for the drowsiness level. For example, when the drowsiness action is detected in the situations C1 to C4 (shown above), the control device 50 calculates the higher reliability.

As other examples that the control device 50 calculates the higher reliability according to the view point P3, when the drowsiness action corresponding to the D0 or D1 drowsiness level is detected right after starting to drive, when the drowsiness action corresponding to the D0 or D1 drowsiness level is detected near an emergency vehicle, when the vehicle is zigzag running and the drowsiness action corresponding to the drowsiness level above D2 is detected, and the like.

The drowsiness point may be changed according to the calculated reliability as follows.

Assume the reliability is calculated with a value from 0 to 1. Here, the closer the value is to 0, the lower the reliability is, and the closer the value is to 1, the higher the reliability is. And, the drowsiness point to be accumulated in the accumulation process is multiplied by the reliability.

For example, consider the case where the drowsiness point is given as shown in FIG. 4. In this case, when the reliability for the D2 drowsiness level is 0.8, the drowsiness point to be accumulated in the accumulation process is 1.6. In the same way, when the reliability for the D2 drowsiness level is 0.4, the drowsiness point to be accumulated in the accumulation process is 0.8. That is, the lower the reliability is, the lower the drowsiness point to be accumulated is.

As described above, calculating the reliability for the drowsiness level and changing the drowsiness point to be accumulated according to the reliability makes it possible to suppress influence of the misestimating of the drowsiness level and suppress giving the drowsiness sign notice at unnecessary timing. As a result, it is possible to suppress the annoyance sense to the driver.

What is claimed is:

1. A drowsiness sign notification system that gives a drowsiness sign notice to a driver that shows a drowsiness sign,
the drowsiness sign notification system comprising:
a driver monitor configured to detect a driver state being a state of the driver; and
a controller configured to provide notification via an HMI unit based on the driver state, wherein the controller is configured to:
execute a drowsiness level estimation process in which a drowsiness level of the driver is estimated based on the driver state from a plurality of drowsiness levels, each of which shows a degree of drowsiness and is classified by the degree of drowsiness by detecting a drowsiness action from among a plurality of detectable drowsiness actions, each drowsiness action corresponding to a single discrete drowsiness level;
execute an accumulation process in which a drowsiness point that is a numerical value corresponding to the discrete drowsiness level estimated in the drowsiness level estimation process is accumulated; and
execute a drowsiness sign determination process in which it is determined that the driver shows the drowsiness sign when an accumulation value of the drowsiness point calculated in the accumulation process exceeds a predetermined threshold;
wherein:
the accumulation process comprises accumulating the drowsiness point sequentially at predetermined time intervals;
the drowsiness point is negative if the driver has no signs of drowsiness;
when the accumulated drowsiness points are negative, they are set to zero; and
the predetermined threshold is set to be smaller than a drowsiness point corresponding to a drowsiness level that means the driver has no drowsiness.

2. The drowsiness sign notification system according to claim 1,
wherein, in the drowsiness level estimation process, a drowsiness action is corresponded to each of the discrete drowsiness levels,
wherein the controller is further configured to:
detect the drowsiness action corresponding to respective discrete drowsiness levels based on the drowsiness state; and when the drowsiness action is detected, estimate the drowsiness level of the driver as the drowsiness level corresponding to the detected drowsiness action.

3. The drowsiness sign notification system according to claim 2,
wherein, in the drowsiness level estimation process, the controller is further configured to:
detect at the top priority the drowsiness action corresponding to the discrete drowsiness level that means the driver has no drowsiness, after that, detect the drowsiness action in the order of the drowsiness level with the higher degree of drowsiness.

4. The drowsiness sign notification system according to claim 1,
wherein the controller is further configured to:
store a frequency distribution of the drowsiness level estimated in the drowsiness level estimation process; and
dynamically change the drowsiness point corresponding to the drowsiness level based on the frequency distribution.

5. The drowsiness sign notification system according to claim 1,
wherein the controller is further configured to:
calculate a reliability for the drowsiness level estimated in the drowsiness level estimation process; and
change the drowsiness point to be accumulated in the accumulation process based on the calculated reliability.

* * * * *